US012758371B2

(12) United States Patent
Choi et al.

(10) Patent No.: US 12,758,371 B2
(45) Date of Patent: Oct. 13, 2026

(54) METHOD FOR USING INTEGRATED LIBRARY

(71) Applicant: MEDIT CORP., Seoul (KR)

(72) Inventors: Won Hoon Choi, Seoul (KR); Ho Taik Lee, Seongnam-si (KR)

(73) Assignee: MEDIT CORP., Seoul (KR)

( * ) Notice: Subject to any disclaimer, the term of this patent is extended or adjusted under 35 U.S.C. 154(b) by 787 days.

(21) Appl. No.: 17/857,070

(22) Filed: Jul. 4, 2022

(65) Prior Publication Data

US 2022/0331076 A1 Oct. 20, 2022

Related U.S. Application Data

(63) Continuation-in-part of application No. PCT/KR2020/019476, filed on Dec. 31, 2020.

(30) Foreign Application Priority Data

Jan. 3, 2020 (KR) ........................ 10-2020-0000560

(51) Int. Cl.

*A61C 13/00* (2006.01)
*A61C 8/00* (2006.01)
*G16H 10/60* (2018.01)
*G16H 30/20* (2018.01)

(52) U.S. Cl.

CPC .......... *A61C 13/0004* (2013.01); *A61C 8/009* (2013.01); *G16H 10/60* (2018.01); *G16H 30/20* (2018.01)

(58) Field of Classification Search

CPC ............................ A61C 8/009; A61C 13/0004
See application file for complete search history.

(56) References Cited

U.S. PATENT DOCUMENTS

2009/0042167 A1* 2/2009 Van Der Zel ........ A61C 9/0053 433/172
2009/0319068 A1* 12/2009 Sager ....................... A61C 5/20 706/14
2015/0282904 A1* 10/2015 Fisker ................ A61C 13/0004 700/98

(Continued)

FOREIGN PATENT DOCUMENTS

KR 10-1632373 B1 6/2016
KR 10-2018-0096138 A 8/2018

(Continued)

OTHER PUBLICATIONS

International Search Report mailed Jun. 11, 2021 for PCT/KR2020/019476 and its English translation.

*Primary Examiner* — Nicholas D Lucchesi

(57) ABSTRACT

A method for using an integrated library according to the present invention is characterized in that when a user selects a target position, an abutment to be applied to an oral cavity of a patient is loaded, and when an abutment model is selected in a database thereof, margin line data linked with the selected abutment model can be displayed together. In addition, the margin line data is not only simply displayed in a thumbnail displaying step, but also can be linked with oral data to be used together. The margin line data can also be edited so as to have a more appropriate form according to the user's need and be stored, such that the existing margin line data can be substituted with edited margin line data.

7 Claims, 10 Drawing Sheets

(56) References Cited

U.S. PATENT DOCUMENTS

| | | | | |
|---|---|---|---|---|
| 2018/0000569 | A1* | 1/2018 | Fisker | G06F 30/20 |
| 2022/0327795 | A1* | 10/2022 | Song | G16H 30/40 |
| 2023/0293274 | A1* | 9/2023 | Choi | A61C 13/0004 433/215 |

FOREIGN PATENT DOCUMENTS

| | | | |
|---|---|---|---|
| KR | 10-1911693 | B1 | 1/2019 |
| KR | 10-2019-0037807 | A | 4/2019 |
| KR | 10-2019-0074062 | A | 6/2019 |
| KR | 10-2033249 | B1 | 10/2019 |

* cited by examiner

METHOD FOR USING INTEGRATED LIBRARY

CROSS-REFERENCE TO RELATED APPLICATIONS

This application is a Continuation-In-Part application of International Application No. PCT/KR2020/019476, filed Dec. 31, 2020, which claims the benefit of Korean Patent Application No. 10-2020-0000560, filed Jan. 3, 2020 in the Korean Intellectual Property Office, the disclosures of which are incorporated herein in their entirety by reference.

TECHNICAL FIELD

The present disclosure relates to a method for using an integrated library and, more particularly, to a method for using an integrated library to use abutment model data stored in a library together with data about a margin line.

BACKGROUND ART

In the field of dental prosthesis treatment, conventionally, dental treatment was performed by taking an impression using alginate, obtaining a plaster model, and manufacturing and providing a prosthesis necessary for a patient. However, in the process of taking an impression using such a solid, the patient easily felt a sense of foreign body, and there was an inconvenience of feeling a sense of vomiting according to the feeling of the foreign body. In addition, the prosthesis manufactured by this process has inaccuracy in dimensions and positions of teeth, gingiva (gum), etc. inside the oral cavity, so there is a risk of providing an inaccurate prosthetic treatment to the patient. This may cause prolonged treatment of a patient or deteriorated patient's oral condition due to incorrect treatment.

A three-dimensional (3D) scanning technology is used in order to solve the patient's discomfort caused by the above-mentioned impression taking using alginate and to provide a patient-specific prosthetic treatment. 3D scanning is used to acquire precise data on the actual patient's oral cavity either when requiring digital data acquisition of a sample to which a prosthesis is applied to a plaster model, or by directly scanning the patient's oral cavity. Data acquired through 3D scanning can be stored for a long time in the form of digital data, and the position, shape, and angle of the prosthesis can be variously applied or changed for the corresponding model.

DISCLOSURE

Technical Problem

An embodiment of the present disclosure is to provide a method of using an integrated library that allows margin line data to be applied and displayed together with abutment model data loaded in a library.

The objective of the present disclosure is not limited to the aforementioned description, and other objectives not explicitly disclosed herein will be clearly understood by a person having ordinary skill in the art from the description provided hereinafter.

Technical Solution

A method of using an integrated library according to the present disclosure may include: a model selection step of selecting a 3D abutment model to be applied by a user from 3D abutment model database; a model display step of displaying the 3D abutment model on an library user interface; a margin line registration step of registering margin line data in the 3D abutment model; a database storage step of storing the 3D abutment model with the margin line data registered therein in the 3D abutment model database; a model selection step of selecting the 3D abutment model with the margin line data registered therein from the 3D abutment model database; and a model loading step of loading the 3D abutment model with the margin line data registered therein on a scan user interface on which a 3D oral model is displayed.

In addition, the 3D abutment model database may be displayed on the library user interface.

Also, the margin line data may be automatically generated to correspond to the 3D abutment model on the library user interface.

Also, the margin line data may be registered in an editable form.

Also, the 3D abutment model may be disposed at a target position corresponding to the 3D abutment model in the 3D oral model.

On the other hand, a method of using an integrated library according to another embodiment of the present disclosure may include: a library loading step of loading 3D abutment model database on a user interface; a model selection step of selecting a 3D abutment model to be applied by a user from the 3D abutment model database loaded in the library loading step; a margin line data registration step of registering margin line data in the 3D abutment model selected in the model selection step; and a database storage step of storing the 3D abutment model with the margin line data registered therein in the 3D abutment model database.

Also, the margin line data may be registered in an editable form.

In addition, the method may further include: a margin line editing step of editing the margin line data; a re-registration step of registering the edited margin line data in the 3D abutment model; and a corrected database storage step of storing the 3D abutment model with the edited margin line data registered therein in the 3D abutment model database.

In addition, the margin line registration step and the re-registration step may be performed on a library user interface, and the 3D abutment model with the margin line data registered therein may be loaded at a specific position of a 3D oral model so as to be displayed on the scan user interface.

In addition, the 3D abutment model may be obtained by scanning a real abutment before implantation in an oral cavity or through CAD design.

In addition, the margin line registered in the margin line registration step may be generated automatically according to curvature information of the margin line of the 3D abutment model or generated by a user's editing.

On the other hand, a method of using an integrated library according to still another embodiment of the present disclosure may include: a library loading step of loading 3D abutment model database corresponding to a target position on a user interface; a model selection step of selecting a 3D abutment model to be applied by a user from the 3D abutment model database loaded in the library loading step; and a thumbnail display step of displaying the 3D abutment model selected in the model selection step together with associated margin line data on the user interface.

The method may further include: a target position selection step of selecting, by a user, the target position from a list section on target positions in a maxilla or a submaxilla on the user interface.

In addition, the method may further include an automatic margin line designation step of auto-tracking the margin line data depending on the 3D abutment model.

In addition, in the automatic margin line designation step, the margin line may be automatically generated depending on curvature information of the margin line of the 3D abutment model.

In addition, the margin line data may be modified by a user's manipulation on the user interface.

In addition, the margin line data modified by the user's manipulation may be stored to substitute the existing margin line data.

Also, the margin line data may be determined by additionally considering color information in the abutment model.

In addition, the user interface may be a library user interface including a thumbnail display section to allow for generation and editing of the margin line for the 3D abutment model displayed on the thumbnail display section on the library user interface.

Advantageous Effects

According to the method of using the integrated library, since the abutment model data loaded in the library is displayed and applied together with the associated margin line data, it is convenient that there is no need to newly draw a margin line every time the abutment model is applied.

In addition, since the margin line data may be automatically generated according to the shape of the abutment as needed, there is an advantage that a user can easily obtain high-accuracy margin line data without manually drawing the margin line.

In addition, the margin line data may not be fixed data, but may be corrected or modified according to the user's needs, and the existing margin line data can be replaced by storing the modified information. Accordingly, there is an advantage that more precise margin line information can be stored, and precise prosthetic treatment can be performed on a patient.

In addition, the margin line data can be generated or edited not only on the scan user interface screen on which the 3D oral model is displayed, but also directly on the library user interface screen including the target position list section, the abutment list section, and the thumbnail display section, providing an advantage of allowing a user to conveniently generate or edit a margin line.

BEST MODE

Figure 1:
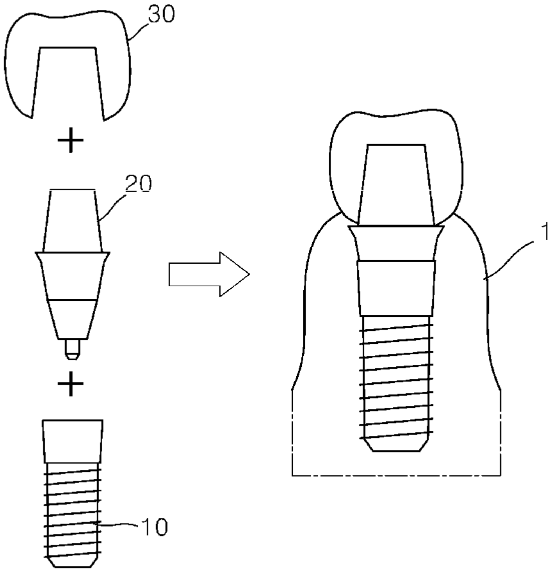
FIG. 1 is a diagram illustrating an abutment in a method of using an integrated library according to the present disclosure.

Hereinafter, embodiments of the present disclosure will be described in detail with reference to the accompanying drawings. When elements in the drawings are designated with reference numerals, like elements may be designated with like reference numerals although the elements are shown in different drawings. Further, in the following description of embodiments of the present disclosure, detailed descriptions of well-known components and functions incorporated herein will be omitted when it is determined that the description may make the subject matter in some embodiments of the present disclosure rather unclear.

Terms, such as "first", "second", "A", "B", "(a)", or "(b)" may be used to describe elements of embodiments of the present disclosure. Each of these terms is not used to define the essence, order, sequence, etc. of the corresponding element, but is used merely to distinguish the corresponding element from other elements. Unless otherwise defined, all terms used herein including technological or scientific terms have the same meanings as those generally understood by those skilled in the art. Terms defined in generally used dictionary shall be construed that they have meanings matching those in the context of the related art, and shall not be construed in ideal or excessively formal meanings unless they are clearly defined in the present application.

On the other hand, in describing the present disclosure, registering margin line data in a 3D abutment model means that the 3D abutment model is displayed together with the margin line data associated therewith.

FIG. 1 is a diagram illustrating an abutment in a method of using an integrated library according to the present disclosure.

Referring to FIG. 1, a dental implant crown operation may mean an operation that in a state in which a damaged tooth is extracted in a patient's oral cavity, can provide a substitute for the damaged tooth. Providing the substitute means that an artificial tooth is implanted to substitute a natural tooth (usually a permanent tooth).

A dental implant crown may be divided into three main components. One is a fixture 10 that is formed to have, on its outer peripheral surface, the shape of a rotary screw, which is screwed into and fastened to the gum (gingiva, 1). The fixture 10 is a structure that corresponds to the root of a natural tooth, and may be firmly fixed to the alveolar bone. In addition, the fixture 10 may be provided with an inner cavity on the side opposite to the rotary screw to be screwed toward the gingiva 1. The cavity formed in the fixture 10 may be combined with an object having a corresponding protrusion.

Figure 2:
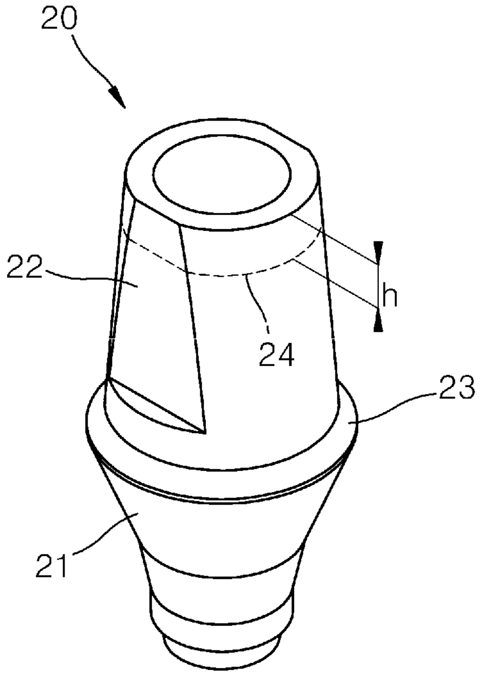
FIG. 2 is a perspective view illustrating an actual model of the abutment loaded as library data in the integrated library using method according to the present disclosure.

FIG. 2 is a perspective view illustrating an actual model of the abutment loaded as library data in the integrated library using method according to the present disclosure.

Referring to FIGS. 1 and 2, one end of an abutment 20 may be fitted into the cavity of the fixture 10. An outer circumferential surface of one end of the abutment 20 fitted into the cavity of the fixture 10 may have the same shape as an inner circumferential surface of the cavity of the fixture 10. On the other hand, the diameter of the abutment 20 may increase from one end that is fitted into the cavity of the fixture 10 toward the other end. This allows the abutment 20 to be coupled in closer contact with the gum. As described above, the portion whose diameter increases from one end to the other end in the longitudinal direction is called a cuff part 21, which may be selected and used by a user by comprehensively taking the patient's gingival height (G/H) and the size of a space left in the gum after the tooth extraction into consideration.

In addition, the abutment 20 further includes a margin line part 23 formed continuously with the cuff part 21 to have a reduced diameter in one longitudinal direction. The margin line may be a portion where the abutment 20 is exposed from the gum, and this portion acts as a key element when the abutment is subsequently covered by a crown.

In addition, a post part 22 may be formed to extend in one longitudinal direction continuously with the margin line part 23. For example, the post part 22 may have a cylindrical shape, and the diameter of the post part 22 may be smaller than that of the margin line connected to the cuff part 21. However, the post part 22 may not have a perfect cylindrical shape, but may have a truncated cone shape in which the diameter of the cross section decreases from the lower portion to the upper portion of the post part 22. The post part 22 may have any shape so long as it is suitable for the inside of the patient's oral cavity and the crown 30 to be described later can be easily coupled thereto.

On the other hand, the margin line included in the margin line part 23 corresponds to a circumferential boundary with the crown 30 that is an artificial tooth portion when coupled to the abutment. That is, since the margin line is used as a coupling reference when the crown is coupled to a tooth (or abutment), the margin line needs to be accurately set. In order for accurate coupling between the tooth (or abutment) and the crown 30, the margin line needs to be formed to correspond to the shape of the tooth or abutment 20. If the margin formation between the abutment 20 and the crown 30 is not good, a gap may occur during the coupling process between the abutment 20 and the crown 30, so that the coupling force of the crown 30 may be weakened. In addition, due to the problem of the margin line, saliva or impurities penetrate through the gap formed between the abutment 20 and the crown 30, thereby increasing the likelihood of caries occurring, and as a result, additional treatment may be required. Therefore, it is necessary to precisely set the margin line and to manufacture a crown that accurately matches the margin line.

FIGS. 3A and 3B are photographs illustrating a cord-winding operation for checking a margin line of the abutment implanted in a patient's gingiva.

Figure 3:
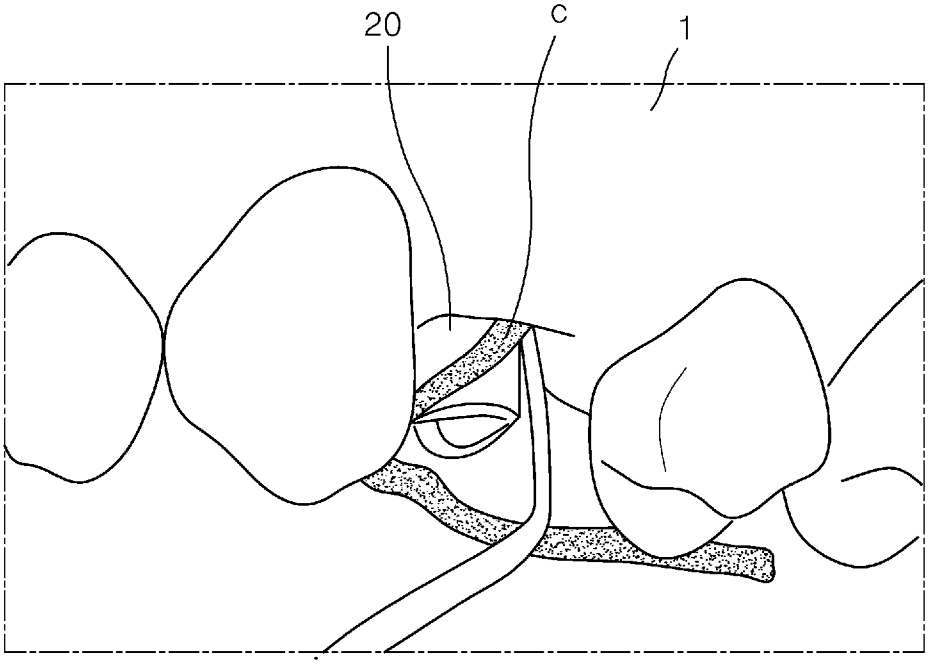
FIGS. 3 and 4 are photographs illustrating a cord-winding operation for checking a margin line of the abutment implanted in a patient's gingiva.
Figure 4:
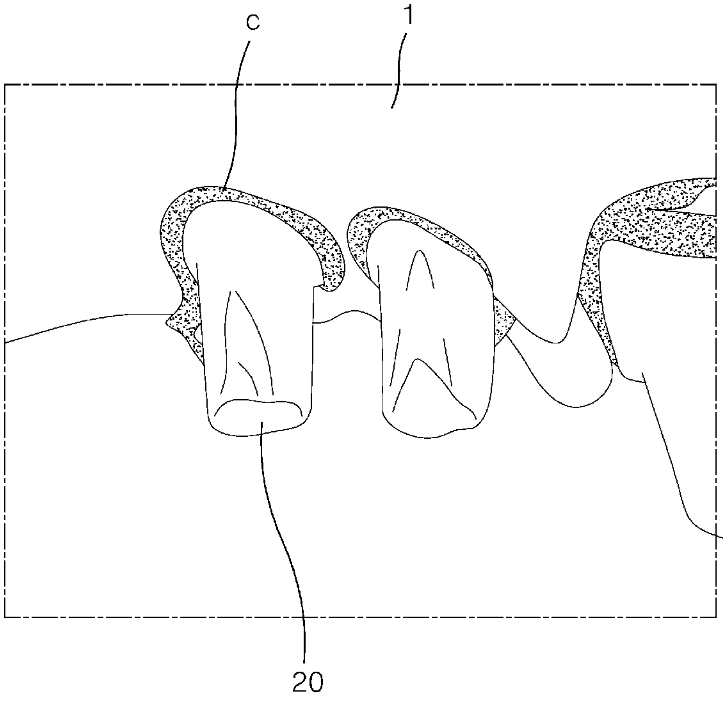

Referring to FIGS. 3 and 4, a conventional method used to set the margin line is illustrated. Conventionally, in order to obtain contour data for the margin line, a portion of an outer circumferential surface of an abutment 20 implanted into the gingiva is wound with a cord C so that the margin line is clearly visible, a prosthesis for which such a cord-winding operation is completed is photographed (or scanned), and then a 3D scanner user (usually a dentist who performs dental activity and treatment) manually draws the margin line directly on a User Interface (UI) while checking the boundary between the gingiva 1 and the abutment 20 with the naked eye.

Drawing the margin line after performing the cord C—winding operation on the implanted abutment 20 as described above requires a lot of work time, and when the abutments 20 are implanted for many patients, there is a problem in that the cord C—winding operation and the margin line—drawing operation are required for all of the implanted abutments 20. In addition, winding the cord C around the outer circumferential surface of the abutment 20 that has already been implanted requires the insertion of the cord C into the gap between the gingiva 1 and the abutment 20, which causes additional pain to the patient. In addition, there is a risk of causing another disease to the patient due to residue of cord by-product and infiltration of saliva or foreign substances, etc. during the insertion and removal of the cord C.

In order to solve these problems, the present disclosure may propose a method of using an integrated library. Through the integrated library using method, accurate margin line data that can be used repeatedly can be used while minimizing the user's inconvenience to perform the cord-winding operation every time an abutment is implanted into the patient's gingiva.

Figure 5:
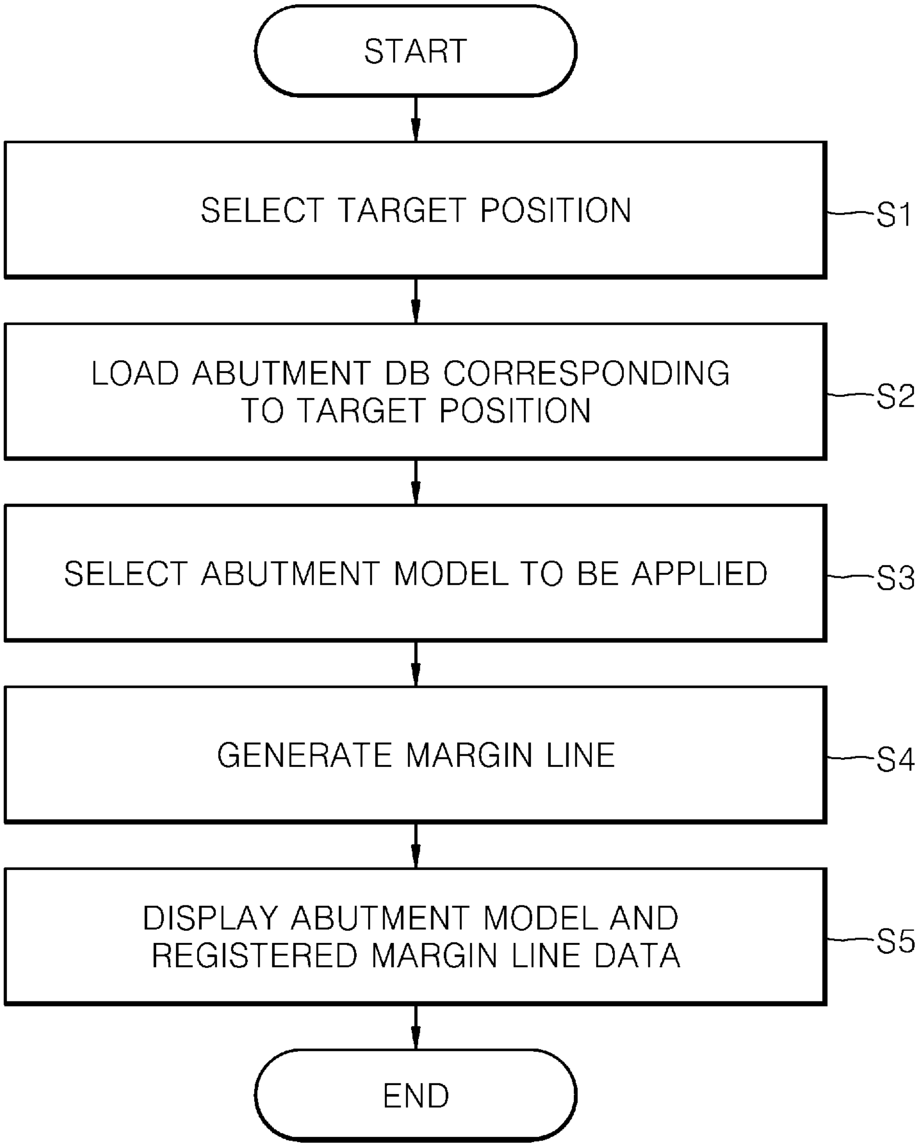
FIG. 5 is a flowchart illustrating a method of using an integrated library according to the present disclosure.
Figure 6:
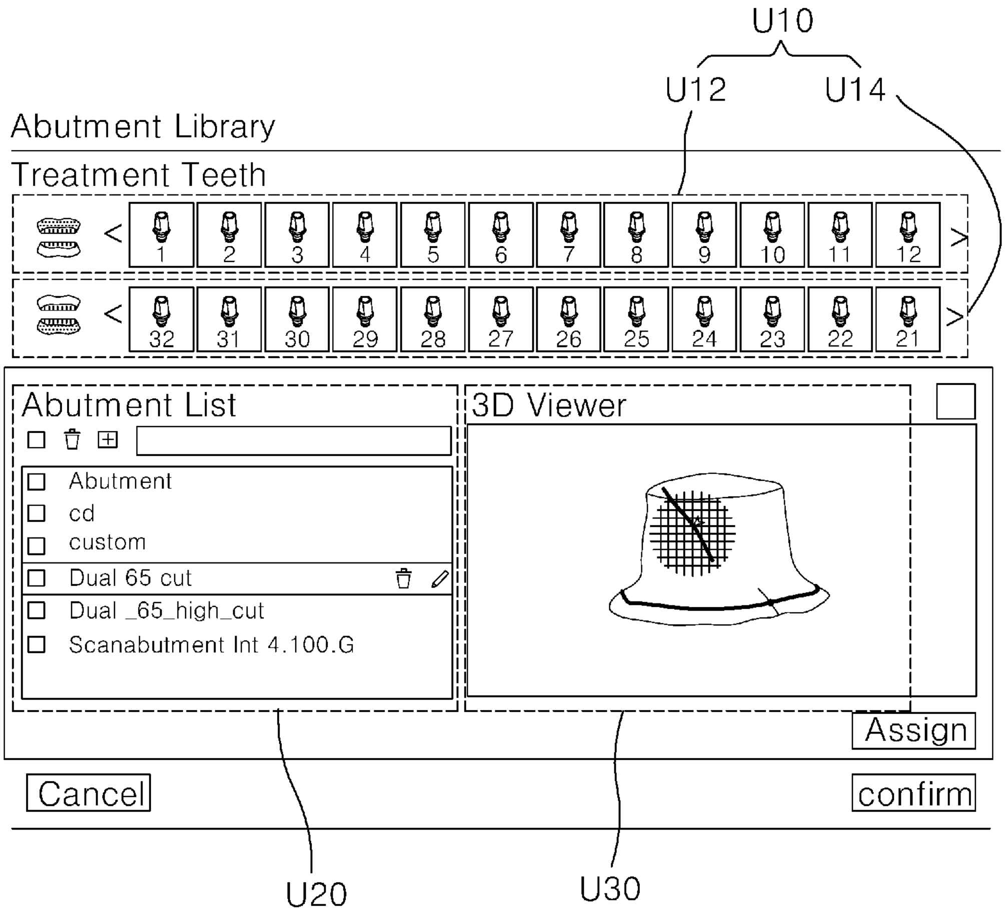
FIG. 6 is a library user interface screen provided in the integrated library using method according to the present disclosure.

FIG. 5 is a flowchart illustrating a method of using an integrated library according to the present disclosure, and FIG. 6 is a library user interface screen provided in the integrated library using method according to the present disclosure.

The integrated library using method according to the present disclosure may include a target position selection step S1 of selecting, by a user, a target position from a list section U10 for target positions included in a maxilla or a submaxilla on a user interface. Referring to FIGS. 5 and 6, a tooth model is shown with the title 'Treatment Teeth' on the upper side of the user interface, and below the title, a maxillary data part U12 in which the maxilla including the upper teeth is displayed in an activated state, and a submaxillary data part U14 in which the submaxilla including the lower teeth is displayed in an activated state may be disposed in first and second rows, respectively.

The list section U10 for target positions displays the positions of all teeth of a person. Here, since a person can have up to 32 teeth, the number of target positions may be displayed in the list section U10 for target positions such that teeth Nos. 1 to 16 are arranged in the maxillary data part U12 and teeth Nos. 17 to 32 are arranged in the submaxillary data part U14. The user may select and click, among the target positions, a specific target position, at which the abutment to be applied to oral model data is to be placed, through target position buttons arranged on the list section U10 for target positions. Meanwhile, the teeth number may be assigned according to a universal numbering system, but this is only an example. That is, the method of assigning the teeth number is not limited to the universal numbering system, and the present disclosure may employ various teeth assignment methods such as World Dental Federation Notation (FDI) method, Palmer notation method, etc.

However, although the foregoing has illustrated that a person can have 32 teeth, the present disclosure is not limited to the number of teeth. That is, the method of using the integrated library according to the present disclosure may be applied even when a person has 28 teeth, and the number of teeth applied on the user interface may be adjusted according to a user's manipulation.

Meanwhile, when the user selects and clicks a target position from the list section U10 for target positions displayed on the user interface, 3D abutment 20 model database corresponding to the selected target position may be loaded on the user interface (library loading step, S2). According to the library loading step S2, the data for the 3D abutment 20 models may be provided in an abutment list section U20 located at the left lower side of the user interface. In this case, the data listed in the abutment list section U20 may be data for 3D abutment 20 models suitable to be arranged at the target position selected in the above-described target position selection step S1. Since only data for the suitable 3D abutment 20 models corresponding to the target position selected by the user are listed, there is an advantage in that the user can quickly retrieve and select the required 3D abutment 20 model without checking all the 3D abutment 20 model data loaded in a library.

On the other hand, when the abutment 20 model database is loaded, the user may select a 3D abutment 20 model to be applied to a patient's oral cavity from the abutment list section U20 (model selection step, S3). At this time, the 3D abutment 20 models loaded from the library may be products that are supplied to dentists, dental technical laboratories, etc. in the form of ready-made products, or customized abutments that are pre-processed according to the user's judgment. On the other hand, the data for the 3D abutment 20 models may be provided by scanning the inside of the patient's oral cavity before the real abutments are implanted in a 3D scanning method, or through CAD design drawing data produced using dimensional information of the real abutments.

When the 3D abutment 20 model is selected in the above-described model selection step S3, 3D modeling data of the selected abutment 20 model may be displayed on a thumbnail display section U30. In addition, when the selected 3D abutment 20 model and margin line data registered in the 3D abutment 20 model and the margin line data registered in the 3D abutment 20 model in the thumbnail display section U30 are provided, the corresponding margin line data may be displayed together on the modeling data of the 3D abutment 20 model. By displaying the modeling data and margin line data of the 3D abutment 20 model together through the thumbnail display section U30, there is an advantage in that the user can check the margin line even before the 3D abutment 20 model is applied to the oral model data.

The above-described target position list section U10, the abutment list section U20, and the thumbnail display section U30 may be displayed on the same user interface. That is, the target position list section U10, the abutment list section U20, and the thumbnail display section U30 may be displayed in the form of a window on a single library user interface.

At this time, oral model data (i.e., a 3D oral model having a 3D shape) may be obtained by scanning the inside of the patient's oral cavity in which the real abutments are implanted, or by scanning the inside of the patient's oral cavity in which the real abutments are not implanted so that the positions of the abutments to be implanted are empty.

On the other hand, although the margin line data may be registered in the existing abutment 20 model, if the margin line data is not registered even though the abutment is a newly pre-processed abutment or a ready-made abutment, it is required to generate the margin line for future use of the margin line data. In this case, margin line data may be generated so that the margin line is auto-tracked according to the 3D abutment 20 model selected in the model selection step S3.

Figure 7:
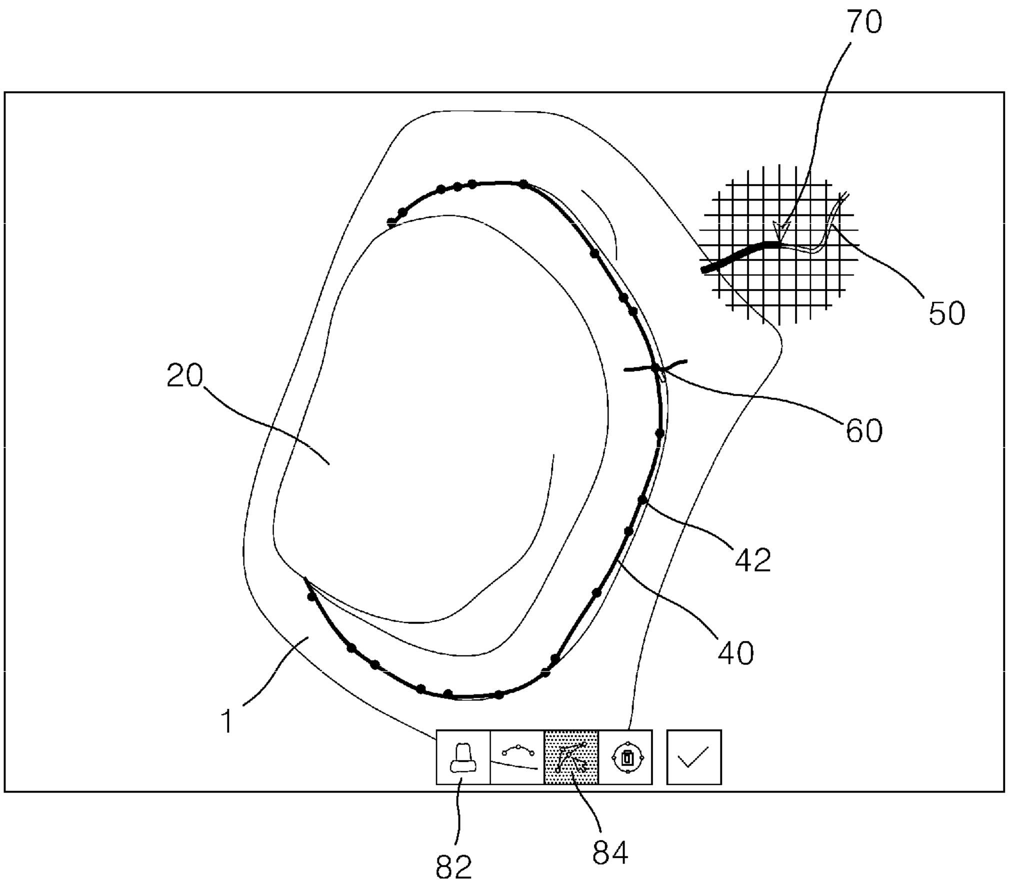
FIG. 7 is a scan user interface screen for generating or modifying a margin line in the integrated library using method according to the present disclosure.

FIG. 7 is a scan user interface screen for generating or modifying a margin line in the integrated library using method according to the present disclosure. Referring to FIGS. 6 and 7, the integrated library using method according to the present disclosure may include a margin line generation step S4. The margin line generation step S4 may mean the step of generating margin line data corresponding to the 3D abutment 20 model. According to the margin line generation step S4, margin line data for the 3D abutment 20 model may be registered in and associated with the 3D abutment 20 model.

Hereinafter, the margin line generation step S4 will be described in more detail.

Figure 8:
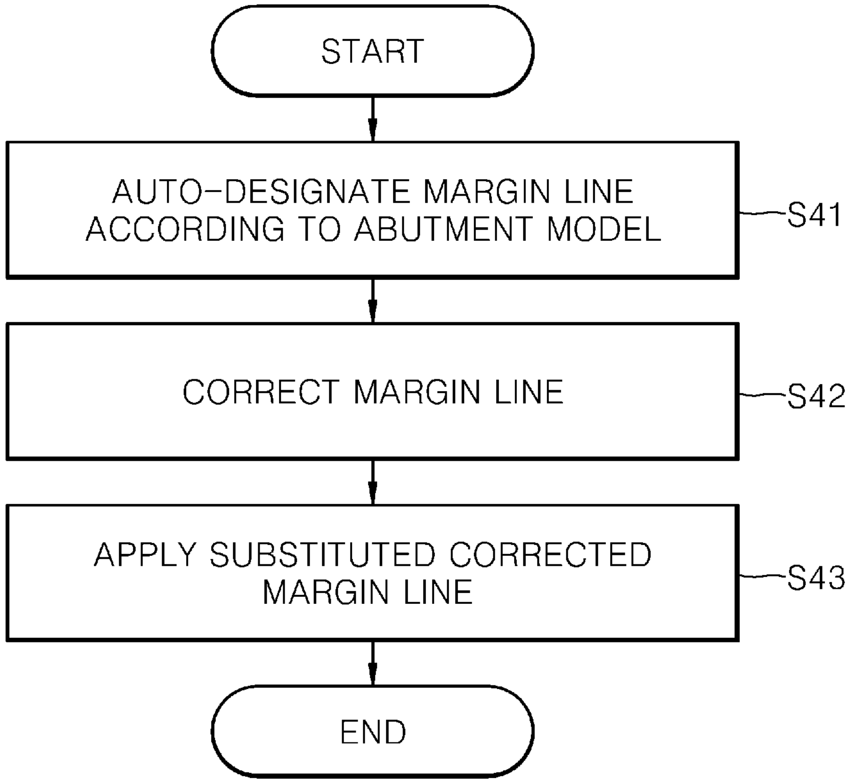
FIG. 8 is a schematic flowchart illustrating steps of editing, modifying, and storing a margin line in the integrated library using method according to the present disclosure.
Figure 9:
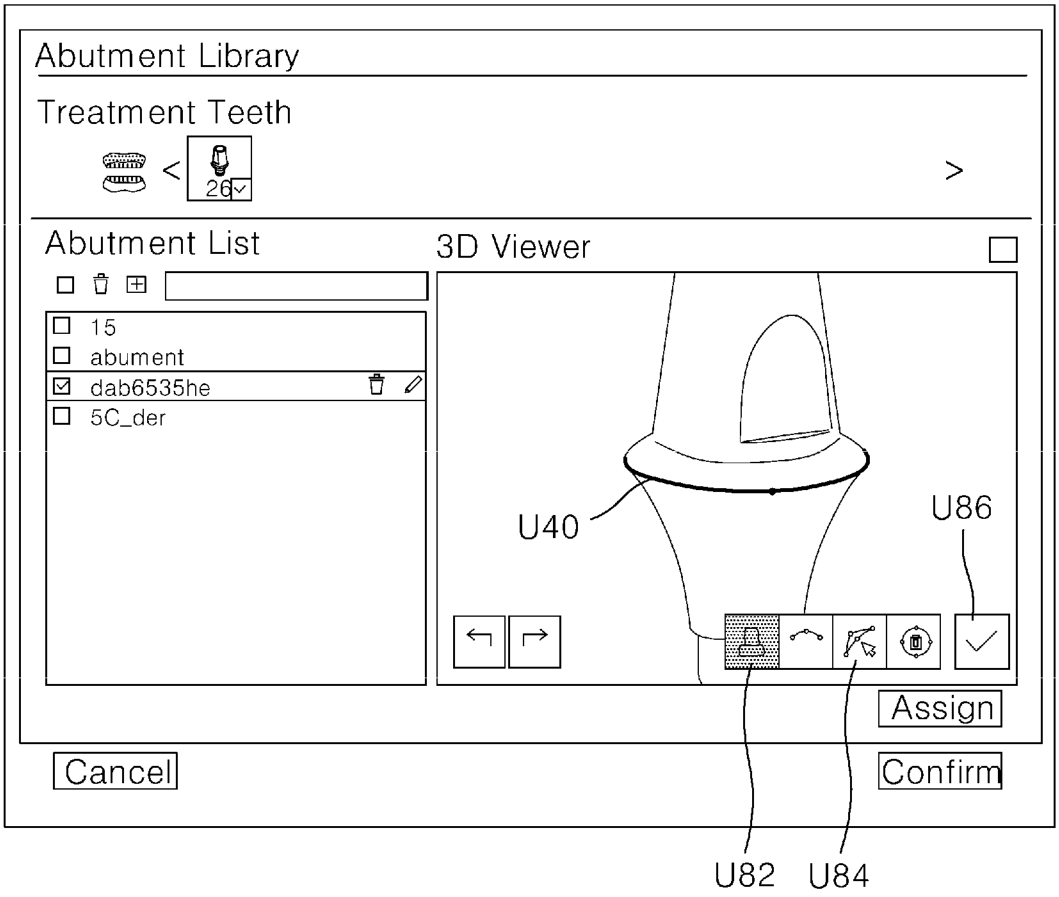
FIG. 9 is a diagram illustrating that a margin line is also displayed on a thumbnail display section of a library user interface screen on a user interface screen provided in the integrated library using method according to the present disclosure.

FIG. 8 is a schematic flowchart illustrating steps of editing, modifying, and storing a margin line in the integrated library using method according to the present disclosure, and FIG. 9 is a diagram illustrating that a margin line is also displayed on a thumbnail display section on a user interface screen provided in the integrated library using method according to the present disclosure.

Referring to FIGS. 6 to 9, when the user sets a margin point 42 in a cross section of the 3D abutment 20 model on a scan user interface screen different from the above-described library user interface, the margin line 40 may be automatically set based on curvature information of the abutment 20 and the gingiva 1 corresponding to the area within a certain distance about the margin point 42, and the colors of the abutment line and the gingiva line (automatic margin line designation step, S41). In order to automatically draw the margin line 40, the user clicks an automatic margin line generation button 82 and then selects one or more margin points 42 to serve as a reference for the margin line 40. When one or more margin points 42 are selected, a processor may generate curvature information obtained by vertically cutting 3D scan data for the surrounding area with respect to the margin points 42 in order to auto-track the margin line 40. Such curvature information may be expressed together with ae mini-map cursor 70 indicating the current position in the form of the curvature mini-map 50 in grid coordinates.

On the other hand, when one or more margin points 42 are selected, the margin line 40 may be automatically generated by selecting and connecting portions having the largest curvature change in a partial range of the selected margin point 42. In this way, the margin line 40 may be automatically generated, and data for the generated margin line 40 may be registered in the 3D abutment 20 model. In addition, when data for the margin line 40 is registered in the 3D abutment 20 model, the margin line 40 data is stored in the database so as to be associated with the 3D abutment 20 model, and when the corresponding 3D abutment 20 model is subsequently loaded from the library, the margin line 40 data may also be loaded together. In this way, by making the abutment 20 model data and the margin line 40 data associated with each other, the patient's inconvenience to obtain the margin line 40 data whenever the abutment 20 is implanted for the patient may be reduced.

Although the automatic margin line designation step S51 according to the selection of the margin point 42 automatically generates the margin line 40 through the curvature information of the abutment 20 model, the margin line 40 may be additionally determined in consideration of color information of the abutment 20 model. That is, the boundary at which color changes in the abutment 20 model may be determined as the margin line 40, so the boundary may be used as reference information for generating the margin line 40, together with the curvature information as described above. Accordingly, the automatic margin line 40 designation step S41 has an advantage of automatically generating a margin line 40 more precisely by considering the curvature information and the color information together.

As described above, although the margin line 40 data may be automatically generated, if the automatically generated margin line 40 is not suitable for the user to provide treatment to a patient, it is required to correct or modify the margin line (which may be called the editing of the previously-generated margin line 40). That is, the margin line 40 data may be registered in an editable form according to the user's needs, because even though the margin line 40 data is registered in the 3D abutment 20 model, the margin line data is not permanently unchangeable data.

The user may correct the margin line 40 data automatically generated or previously registered in the abutment 20 model by clicking the margin line correction button 84 to correct the margin line 40 (margin line correction step, S42). By correcting the margin line 40 data by the user, the automatically generated or previously registered data may be finely corrected, which provides an advantage of enabling more suitable prosthetic treatment for a patient.

On the other hand, the corrected margin line 40 may be registered so as to be associated with the 3D abutment 20 model data and may be stored in the database to substitute the margin line 40 data previously associated with the 3D abutment 20 model data (corrected margin line application step, S43). With the new association of the corrected margin line 40 data with the 3D abutment 20 model data, the margin line 40 data that is more suitable for the 3D abutment 20 model loaded in a library may be registered and stored in an associated manner. Therefore, this provides an advantage that it is possible to provide a precise prosthetic treatment to a patient. The 3D abutment 20 model registered in association with the margin line 40 data may be loaded into a target position of a 3D oral model and then used in manufacturing a crown.

On the other hand, referring to FIG. 8, although the generation or editing of the margin line 40 may be performed in a state in which the overall 3D oral model data is displayed on the scan user interface and the 3D abutment 20 model is loaded into the target position, it is also possible to edit the margin line 40 while checking the 3D abutment 20 model displayed on the thumbnail display section U30 on the library user interface window. In a state in which a margin line U40 that is registered in association with the 3D abutment 20 is displayed on the thumbnail display section U30, and the automatic margin line generation button U82 on the user interface (UI) window is clicked so that the margin line U40 may be automatically displayed through the above-described process, the user may register the margin line 40 data in the 3D abutment 20 model data in a mutually associated manner through the margin line registration button U86. Afterwards, when the corresponding 3D abutment 20 model is selected on the library user interface, the 3D abutment 20 model in which the margin line is registered is loaded on the scan user interface on which the 3D oral model is displayed, so that it is possible to terminate the scanning process without a separate margin line registration process.

Also, if the user tries to edit the automatically generated margin line U40 as needed, the user may edit the margin line by clicking a margin line correction button U84 displayed on the thumbnail display section U30. When the edited margin line 40 is registered by clicking a registration button U86, the previously associated margin line 40 data is substituted and registered by the corrected and edited data, and the substituted margin line 40 data is stored together in the 3D abutment 20 model database, so that when the corresponding 3D abutment 20 model is loaded, the margin line 40 data registered so as to be associated is loaded together, thereby allowing for the provision of a precise prosthesis treatment to a patient. That is, even if the user does not necessarily move to the scan user interface screen to generate or edit the margin line, the margin line may be generated, edited, or registered on the library user interface including the target position list section U10, the abutment list section U20, and the thumbnail display section U30.

In addition, the generated or edited margin line 40 may be displayed on the user interface in association with the 3D abutment 20 model selected in the model selection step S3 (thumbnail display step S5). In this case, the space in which the 3D abutment 20 model and the margin line 40 data are displayed may be a scan user interface. As illustrated in FIG. 7, since the margin line is displayed on the scan user interface, the user can easily check the margin line 40 of the 3D abutment 20 model arranged at the target position.

Meanwhile, the space in which the 3D abutment 20 model and the margin line 40 data are displayed may be a library user interface rather than a scan user interface. As illustrated in FIG. 6 or 9, the 3D abutment 20 model selected from the thumbnail display section U30 of the library user interface and the margin line 40 associated with the model may be displayed together. The user may check the shape of the 3D abutment 20 model and the margin line 40 together in the process of selecting the 3D abutment 20 model, and may edit the margin line 40 on the library user interface.

Hereinafter, a method of using an integrated library according to another embodiment of the present disclosure will be described.

Figure 10:
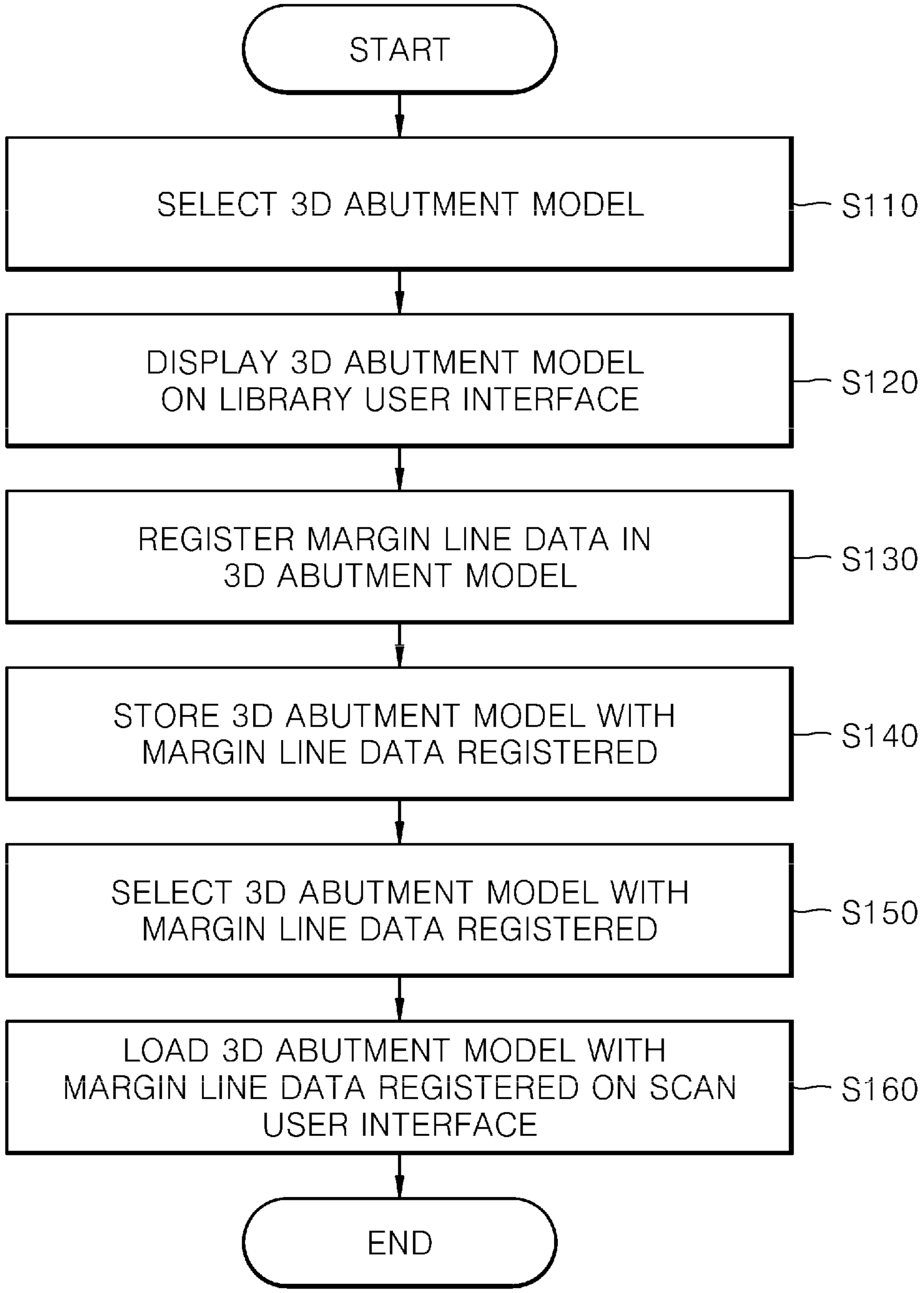
FIG. 10 is a flowchart illustrating a method of using an integrated library according to another embodiment of the present disclosure.

FIG. 10 is a flowchart illustrating a method of using an integrated library according to another embodiment of the present disclosure.

The integrated library using method according to another embodiment of the present disclosure includes: a model selection step S110 of selecting a 3D abutment model to be applied by a user from the 3D abutment model database; a model display step S120 of displaying the 3D abutment model on a library user interface; a margin line registration step S130 of registering margin line data in the 3D abutment model; and a database storage step S140 of storing the 3D abutment model in which the margin line data is registered in the 3D abutment model database.

In the model selection step S110, the 3D abutment model database may be displayed in the form of a list on the library user interface. The user may select a 3D abutment model to be applied to a specific target position from the 3D abutment model database displayed on the library user interface. Meanwhile, the library user interface may selectively display only the 3D abutment model that can be applied to a specific target position by the user's selection.

In the model display step S120, the selected 3D abutment model may be displayed on the library user interface. In this case, the 3D abutment model may be displayed on the thumbnail display section described above. The displayed 3D abutment model may be moved and rotated on the thumbnail display section, and the user can easily visually check the shape of the entire 3D abutment model.

Meanwhile, the method may further include a margin line registration step S130 of registering margin line data in the selected 3D abutment model. The margin line registration step S130 may be performed in a library user interface environment, and as described above, by clicking a predetermined button formed on the thumbnail display section, a margin line corresponding to the 3D abutment model may be automatically generated. As described above, the margin line may be generated in consideration of curvature information and color information of the 3D abutment model. The margin line data may be associated with a corresponding 3D abutment model.

The generated margin line data is registered in an editable form according to the user's needs. The process of editing the margin line data is the same as described above.

When the margin line data is registered in the 3D abutment model, the 3D abutment model including the margin line data may be stored in the 3D abutment model database in the database storage step S140. Accordingly, when the corresponding 3D abutment model is subsequently selected, the margin line data registered in the corresponding 3D abutment model may be displayed together.

Thereafter, a model selection step S150 of selecting the 3D abutment model with the margin line data registered therein from the 3D abutment model database may be performed. For example, when a 3D abutment model is selected on the library user interface, the corresponding 3D abutment model and the registered margin line data may be displayed together on the thumbnail display section. The user may check the registered margin line together with the schematic shape of the 3D abutment model on the library user interface.

When the 3D abutment model with the margin line registered therein is selected, a model loading step S160 may be performed. In the model loading step S160, the 3D abutment model may be loaded on a scan user interface different from the library user interface. At this time, when the user sets a target position on the library user interface or when a 3D abutment model applied only to a specific target position is selected, the 3D abutment model may be loaded at the target position of a 3D oral model displayed on the scan user interface. When the 3D abutment model is loaded on the scan user interface, the registered margin line data may also be loaded. Therefore, the user can easily visually check the state in which the 3D abutment model is applied to the 3D oral model, and can provide a suitable treatment to a patient through the margin line displayed together with the 3D abutment model.

Hereinafter, a method of using an integrated library according to still another embodiment of the present disclosure will be described.

Figure 11:
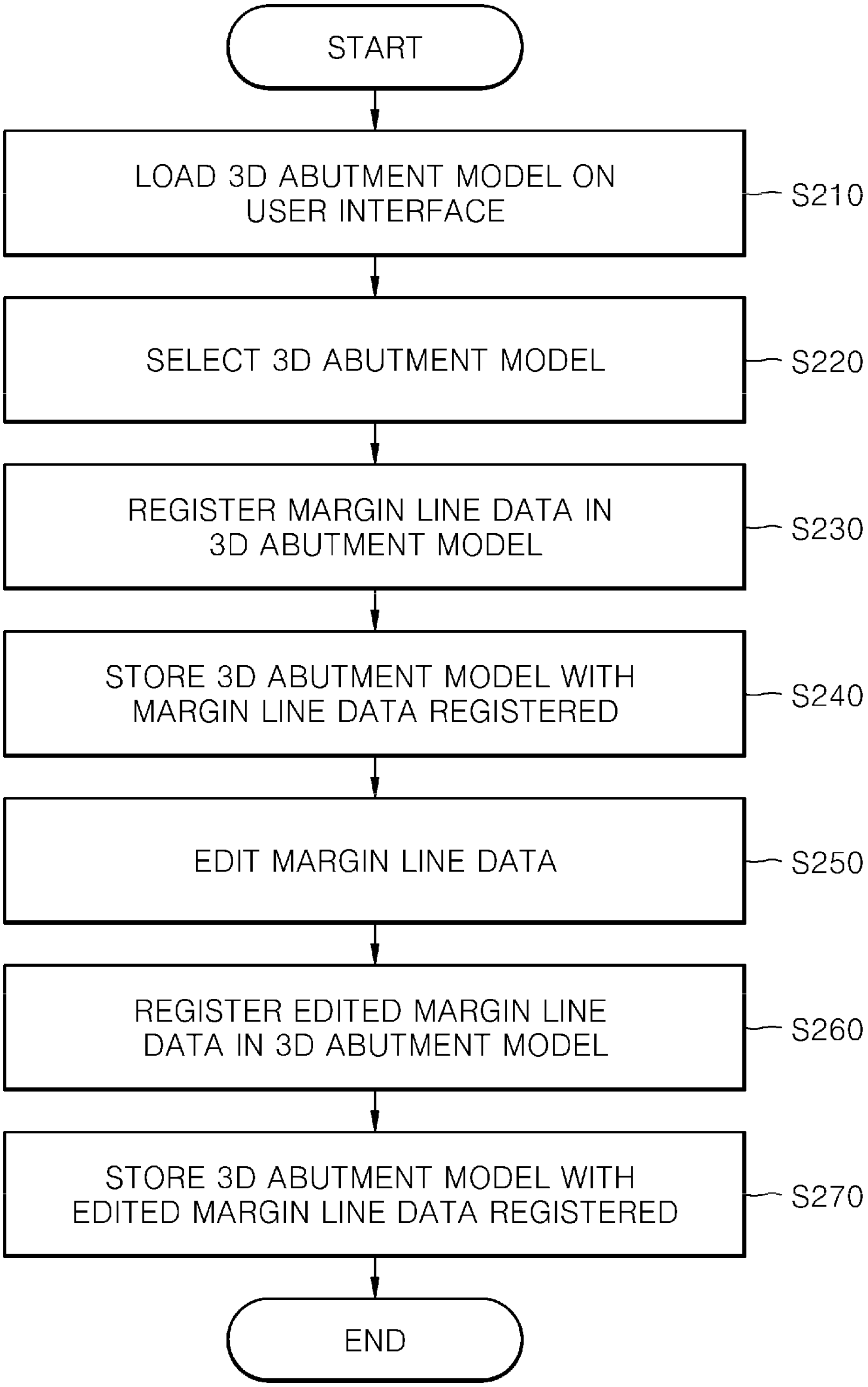
FIG. 11 is a flowchart illustrating a method of using an integrated library according to still another embodiment of the present disclosure.

FIG. 11 is a flowchart illustrating a method of using an integrated library according to still another embodiment of the present disclosure.

Referring to FIG. 11, the integrated library using method according to still another embodiment of the present disclosure may include: a library loading step S210 of loading 3D abutment model database on a user interface; a model selection step S220 of selecting a 3D abutment model to be applied by a user from the 3D abutment model database loaded in the library loading step S210; a margin line registration step S230 of registering margin line data in the 3D abutment model selected in the model selection step S220; and a database storage step S240 of storing the 3D abutment model with the margin line data registered therein in the 3D abutment model database.

In the integrated library using method according to still another embodiment of the present disclosure, the library loading step S210, the model selection step S220, the margin line registration step S230, and the database storage step S240 are performed in the same process performed by the above-described integrated library using method. That is, the 3D abutment model database may be loaded on the library user interface, the 3D abutment model to be applied to the 3D oral cavity by a user may be selected from the database, and margin line data may be automatically generated according to the shape of the selected 3D abutment model and registered so as to be associated with the 3D abutment model. On the other hand, when the 3D abutment model in which the margin line data is registered is stored in the database, the 3D abutment model and the registered margin are displayed together on the library user interface and/or scan user interface when the corresponding 3D abutment model is subsequently selected.

Meanwhile, the integrated library using method according to still another embodiment of the present disclosure may further include a margin line editing step S250 of editing the registered margin line data. The margin line data may be registered in the 3D abutment model in an editable form, and may be corrected according to the user's needs. For example, the user may manually edit the margin line displayed on the thumbnail display section of the library user interface. Editing the margin line may be performed by moving margin points on the margin line, and the margin line editing method is performed as described above.

In addition, the edited margin line data may be registered again in the corresponding 3D abutment model (re-registration step S260). In this case, the edited margin line data may substitute the margin line data before editing, and the user may use a more precise margin line through the edited margin line data. After the re-registration step S260, a corrected database storage step S270 of re-storing the 3D abutment model with the edited margin line data registered therein in the 3D abutment model. In the corrected database storage step S270, the changes in the 3D abutment model with the edited margin line data registered therein may be stored, and then the edited margin line data may also be displayed when the corresponding 3D abutment model is selected or loaded.

Meanwhile, the margin line registration step S240 and the re-registration step S260 may be performed on the library user interface, and the 3D abutment model with the margin line data registered therein may be loaded on the scan user interface. The 3D abutment model may be loaded at a specific position of the 3D oral model displayed on the scan user interface. For example, the 3D abutment model may be loaded at a target position of the 3D oral model to which the 3D abutment model may be applied. The target position may be determined by the user's selection or may be automatically determined according to the type of the 3D abutment model. The user may easily analyze the patient's oral cavity by applying the 3D abutment model to the 3D oral cavity model displayed on the scan user interface. In addition, by checking the margin line of the 3D abutment model loaded at the target position of the 3D oral model, there is an advantage in that it is possible to manufacture a precise prosthesis. In addition, since the margin line may be edited and reset, there is an advantage that reliable data may be obtained, and the user may provide a precise prosthesis to a patient.

Hereinafter, an integrated library system for performing the above-described the integrated library using method will be described.

Figure 12:
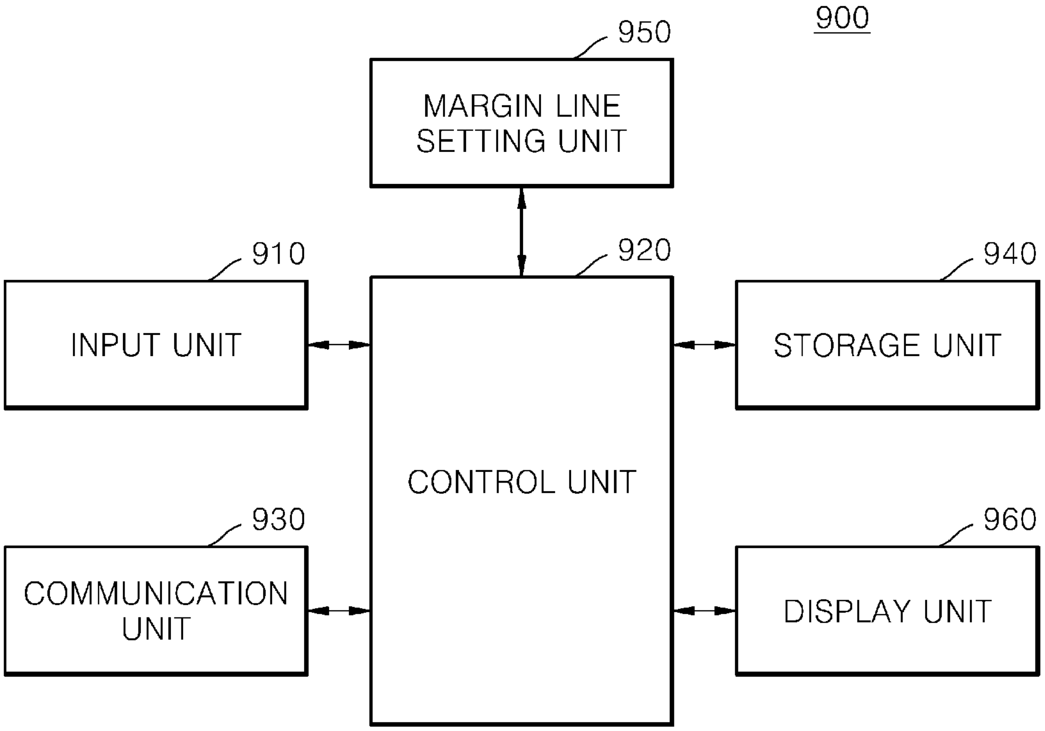
FIG. 12 is a block diagram illustrating an integrated library system 900 performing the integrated library using method according to the various embodiments described above.

FIG. 12 is a block diagram illustrating an integrated library system 900 performing the integrated library using method according to the various embodiments described above.

Referring to FIG. 12, the integrated library system 900 includes an input unit 910. The input unit 910 may be a device capable of receiving a user's input, and may be at least one of a mouse, a keyboard, and a touchpad. The user may select a target position where a 3D abutment model is to be placed, select the 3D abutment model displayed on a user interface screen, or generate or correct a 3D abutment margin line through the input unit 910. In some cases, the input unit 910 may be a 3D scanner capable of scanning a real abutment.

The integrated library system 900 includes a control unit 920. For example, the control unit 920 may be a microprocessor capable of data operation. The control unit 920 may be configured to load the user interface screen on an output unit 960, to load a library including a 3D abutment model database on the user interface screen, to arrange the 3D abutment model selected according to a user's input signal through the input unit 910 at a target position on a scan user interface, to control a margin line setting unit 950 to be described later to generate/correct (edit) a margin line according to a user's input signal through the input unit 910, or to register (or associate) or re-register the generated margin line in (or with) the 3D abutment model and store the same in a storage unit 940 (database).

The integrated library system 900 includes a communication unit 930. The communication unit 930 enables data communication between components constituting the integrated library system 900 using at least one of known communication methods. For example, a communication interface provided by the communication unit 930 may include, but is not limited to, LAN, LTE, WIFI, and the like.

The integrated library system includes a storage unit 940. The storage unit 940 may store a user interface (including a library user interface and a scan user interface), a library including a 3D abutment model database, and margin line data registered in the 3D abutment model. For example, the storage unit 940 may be at least one of known storage media such as a hard disk, RAM, and flash memory.

The integrated library system 900 includes a margin line setting unit 950. The margin line setting unit 950 may generate the margin line on the basis of the curvature information of an abutment and a gingiva, and the color of the abutment line and the gingival line under the control of the control unit 920 according to the margin point set by the user's input. Also, the margin line setting unit 950 may correct (edit) the margin line generated under the control of the control unit 920.

The integrated library system 900 includes an output unit 960. For example, the output unit 960 may be at least one of known visual output devices such as an LCD monitor and an LED monitor. The output unit 960 may visually display information displayed on a library user interface, a scan user interface, and the user interfaces (e.g., information about an abutment list, a thumbnail of 3D abutment models, a margin point, and a margin line registered in the 3D abutment model) under the control of the control unit 920.

The above description is merely illustrative of the technical spirit of the present disclosure, and various modifications and variations will be possible without departing from the essential characteristics of the present disclosure by those skilled in the art to which the present disclosure pertains.

Therefore, the embodiments disclosed in the present disclosure are intended not to limit, but to describe the technical spirit of the present disclosure, and the scope of the technical spirit of the present disclosure is not limited to the disclosed embodiments. The protection scope of the present disclosure should be construed by the following claims, and all technical ideas within the scope equivalent thereto should be construed as being included in the scope of the present disclosure.

| [Description of Reference Signs] | |
|---|---|
| 1: | Gingiva |
| 10: | Fixture |
| 20: | Abutment |
| 21: | Cuff part |
| 22: | Post part |
| 23: | Margin line part |
| 30: | Crown |
| 40: | Margin line |
| 42: | Margin point |
| 50: | Curved mini-map |
| 60: | Color mini-map |
| 70: | Mini-map cursor |
| 82: | Automatic margin line generation button |
| 84: | Margin line correction button |
| C: | Cord |
| U10: | Target position list section |
| U12: | Maxillary data |
| U14: | Submaxillary data |
| U20: | Abutment list part |
| U30: | Thumbnail display section |
| U40: | Margin line |
| U82: | Automatic margin line generation button |
| U84: | Margin line correction button |
| U86: | Margin line registration button |
| S1: | Target position selection step |
| S2: | Library loading step |
| S3: | Model selection step |
| S4: | Margin line generation step |
| S5: | Thumbnail display step |
| S41: | Automatic margin line designation step |
| S42: | Margin line correction step |
| S43: | Corrected margin line application step |
| S110: | Model selection step |
| S120: | Model display step |
| S130: | Margin line registration step |
| S140: | Database storage step |
| S150: | Margin line-registered model selection step |
| S160: | Model loading step |
| S210: | Model loading step |
| S220: | Model selection step |
| S230: | Margin line registration step |
| S240: | Database storage step |
| S250: | Margin line editing step |
| S260: | Re-registration step |
| S270: | Corrected database storage step |

INDUSTRIAL APPLICABILITY

The present disclosure is to provide a method of using an integrated library by registering a margin line in a 3D abutment model and displaying the 3D abutment model together with the registered margin line.

The invention claimed is:

1. A method of using an integrated library, the method comprising:

a model selection step of selecting a 3D abutment model to be applied by a user from 3D abutment model database;

a model display step of displaying the 3D abutment model on a library user interface;

a margin line registration step of registering margin line data automatically generated or edited in the 3D abutment model in the library user interface where the 3D abutment model is displayed thereon;

a database storage step of storing the 3D abutment model with the margin line data registered therein in the 3D abutment model database so as to be associated with the 3D abutment model;

a model selection step of selecting the 3D abutment model with the margin line data registered therein from the 3D abutment model database; and a model loading step of loading the 3D abutment model with the margin line data registered therein on a scan user interface different from the library user interface on which a 3D oral model is displayed.

2. The method of claim 1, wherein the 3D abutment model is disposed at a target position corresponding to the 3D abutment model in the 3D oral model.

3. A method of using an integrated library, the method comprising:

a library loading step of loading 3D abutment model database on a library user interface;

a model selection step of selecting a 3D abutment model to be applied by a user from the 3D abutment model database loaded in the library loading step;

a margin line data registration step of registering margin line data automatically generated or edited in the library user interface where the 3D abutment model is displayed thereon, in the 3D abutment model selected in the model selection step;

a database storage step of storing the 3D abutment model with the margin line data registered therein in the 3D abutment model database so as to be associated with the 3D abutment model; and a model loading step of loading the 3D abutment model with the margin line data registered therein on a scan user interface different from the library user interface on which a 3D oral model is displayed.

4. The method of claim 3, further comprising:

a margin line editing step of editing the margin line data associated with the 3D abutment model;

a re-registration step of registering the edited margin line data in the 3D abutment model; and a corrected database storage step of storing the 3D abutment model with the edited margin line data registered therein in the 3D abutment model database so as to be associated with the 3D abutment model.

5. The method of claim 4, wherein the margin line registration step and the re-registration step are performed on a library user interface, and the 3D abutment model with the margin line data registered therein is loaded at a specific position of a 3D oral model so as to be displayed on the scan user interface.

6. The method of claim 4, wherein the 3D abutment model is obtained by scanning a real abutment before implantation in an oral cavity or through CAD design.

7. The method of claim 3, wherein the margin line registered in the margin line registration step is generated automatically according to curvature information of the margin line of the 3D abutment model or generated by a user's editing.

* * * * *